(12) United States Patent
Horen (10) Patent No.: US 10,702,741 B2
(45) Date of Patent: Jul. 7, 2020

(54) MULTIFUNCTIONAL THERAPY DEVICE

(71) Applicant: Serena R. Horen, Fort Wayne, IN (US)

(72) Inventor: Serena R. Horen, Fort Wayne, IN (US)

( * ) Notice: Subject to any disclaimer, the term of this patent is extended or adjusted under 35 U.S.C. 154(b) by 5 days.

(21) Appl. No.: 15/419,689

(22) Filed: Jan. 30, 2017

(65) Prior Publication Data

US 2018/0214740 A1  Aug. 2, 2018

(51) Int. Cl.
| | | |
|---|---|---|
| *A63B 23/12* | (2006.01) | |
| *A63B 21/00* | (2006.01) | |
| *A63B 21/065* | (2006.01) | |
| *A63B 21/012* | (2006.01) | |
| *A61N 1/36* | (2006.01) | |

(52) U.S. Cl.
CPC ........ *A63B 23/12* (2013.01); *A63B 21/00069* (2013.01); *A63B 21/012* (2013.01); *A63B 21/065* (2013.01); *A63B 21/159* (2013.01); *A63B 21/4035* (2015.10); *A63B 21/4047* (2015.10); *A61N 1/36003* (2013.01); *A61N 1/3603* (2017.08); *A61N 1/36025* (2013.01); *A63B 2213/004* (2013.01)

(58) Field of Classification Search
CPC . A63B 23/00; A63B 23/035; A63B 23/03508; A63B 23/03516; A63B 23/03533; A63B 23/03541; A63B 23/12; A63B 23/1245; A63B 23/1263; A63B 23/1272; A63B 23/1281; A63B 21/012; A63B 21/015; A63B 21/159; A63B 21/40; A63B 21/4023; A63B 21/4027; A63B 21/4035

USPC .................. 607/77, 78; 482/92, 93, 97, 110, 482/114–117, 121, 126, 127

See application file for complete search history.

(56) References Cited

U.S. PATENT DOCUMENTS

| | | | | |
|---|---|---|---|---|
| 3,802,701 | A * | 4/1974 | Good, Jr. ............. | A63B 21/015 482/119 |
| 5,529,552 | A * | 6/1996 | Biedermann ........ | A63B 21/153 482/111 |
| 5,690,590 | A * | 11/1997 | Lo ....................... | A63B 21/0552 482/51 |
| 6,231,484 | B1 * | 5/2001 | Gordon ................. | A63B 69/18 482/51 |
| 7,544,156 | B2 * | 6/2009 | Webber ............. | A63B 21/00181 482/100 |
| 7,625,317 | B2 * | 12/2009 | Stevenson .......... | A63B 22/0002 482/142 |
| D620,540 | S * | 7/2010 | McVay ........................ | D21/668 |

(Continued)

*Primary Examiner* — Ahmed M Farah
(74) *Attorney, Agent, or Firm* — Faegre Drinker Biddle & Reath LLP (57) ABSTRACT

A therapy device aids an occupational therapist in soft tissue recovery and development. The device includes an attachment base which anchors to a table or other support surface, a riser pivotably connected to the base with 2-3 degrees of freedom, and a handle connected to the riser with an additional 2-3 degree of freedom. Each pivotable connection can be adjusted to rotate freely or with a desired level of friction, or can be locked in a desired configuration. Multiple interchangeable handles may be included to adjust the patient-device interface, e.g., unilateral or bilateral engagement. Height adjustments may also be provided. The dual-pivoting design and adjustability of the device facilitates applications for a wide variety of patients with varying therapeutic needs.

15 Claims, 7 Drawing Sheets

(56) References Cited

U.S. PATENT DOCUMENTS

| | | | |
|---|---|---|---|
| 8,500,612 B2* | 8/2013 | Koch | A63B 21/026 |
| | | | 482/129 |
| 8,636,630 B2* | 1/2014 | Morris | A63B 21/00069 |
| | | | 482/117 |
| 8,979,720 B2* | 3/2015 | Brentham | A63B 21/0083 |
| | | | 482/112 |
| 9,050,492 B2* | 6/2015 | Shifferaw | A63B 21/0421 |
| 9,259,606 B2* | 2/2016 | Wolan | A63B 21/0442 |
| 2005/0130814 A1* | 6/2005 | Nitta | A63B 1/00 |
| | | | 482/121 |
| 2009/0017999 A1* | 1/2009 | Halbridge | A63B 21/026 |
| | | | 482/130 |
| 2013/0190146 A1* | 7/2013 | Thomas | A63B 21/0555 |
| | | | 482/121 |

* cited by examiner

MULTIFUNCTIONAL THERAPY DEVICE

BACKGROUND

1. Technical Field

The present disclosure relates to occupational therapy devices, and, in particular, to multifunctional therapy devices for treatment of soft tissues in the upper extremities.

2. Description of the Related Art

Occupational and physical therapists frequently use therapy aids as part of an overall treatment plan to promote a desired patient outcome. Such therapy aids include exercise machines, patient support devices including mats and benches, stretchable resistance bands, and the like. In many cases, such devices are designed to guide a single motion or limited range of motions, in order to target a single muscle or group of muscles. As a result, many therapy facilities employ a collection of devices to enable a physical or occupational therapist to address the needs of each individual patient.

Moreover, the goal of physical and occupational therapy is often to teach or enhance a patient's ability to perform necessary or daily tasks which have been impaired by injury or illness. To this end, several among the collection of therapy devices typically available to a therapist may be used to target various motions or muscle groups involved with the activity being taught to the patient.

What is needed is an improvement over the foregoing.

SUMMARY

The present disclosure provides a therapy device designed to aid an occupational therapist in soft tissue recovery and development. The device includes an attachment base which anchors to a table or other support surface, a riser pivotably connected to the base with 2-3 degrees of freedom, and a handle connected to the riser with an additional 2-3 degrees of freedom. Each pivotable connection can be adjusted to rotate freely or with a desired level of friction, or can be locked in a desired configuration. Multiple interchangeable handles may be included to adjust the patient-device interface, e.g., unilateral or bilateral engagement. Height adjustments may also be provided. The dual-pivoting design and adjustability of the device facilitates applications for a wide variety of patients with varying therapeutic needs, such that the device provides a highly functional yet cost effective solution for a wide variety of patient training scenarios.

In one form thereof, the present disclosure provides a soft tissue therapy device for use with upper extremities of patient, the device having an attachment base including a first base arm having a first longitudinal extent between a first end portion and second end portion thereof, such that the first base arm defines a first base arm axis; a first clamp affixed to the first base arm at the first end portion thereof; a second base arm having a second longitudinal extent between a first end portion and second end portion thereof, such that the second base arm defines a second base arm axis; and a second clamp affixed to the second base arm at the first end portion thereof, the first base arm fixed to the second base arm at their respective second end portions to form an angle between the first and second base arm axes, such that the first and second base arm axes cooperate to define a support plane, the support plane defining an X-Y plane of a Cartesian coordinate system. The device further includes a handle comprising a handle attachment portion defining a handle axis and at least one grip portion spaced from the handle attachment portion; and a riser having a third longitudinal extent defining a riser axis, the riser extending between a lower riser end and an opposed upper riser end. The lower riser end has a lower pivotable connection to the attachment base, the lower pivotable connection defining a neutral riser position in which the riser extends upwardly from the support plane in a Z-direction of the Cartesian coordinate system. The upper riser end has an upper pivotable connection to the handle, the upper pivotable connection defining a neutral handle position in which the handle axis and the riser axis are substantially parallel. The lower pivotable connection has a first degree of freedom in the X-direction and a second degree of freedom in the Y-direction, whereby the riser axis is moveable throughout a first spherical sector centered at the lower pivotable connection, and the upper pivotable connection has a third degree of freedom in the X-direction and a fourth degree of freedom in the Y-direction, whereby the handle axis is moveable throughout a second spherical sector centered at the upper pivotable connection.

In another form thereof, the present disclosure provides a soft tissue therapy device for use with upper extremities of patient, the device having an attachment base including a first base arm having a first longitudinal extent between a first end portion and second end portion thereof, such that the first base arm defines a first base arm axis; a first clamp affixed to the first base arm at the first end portion thereof a second base arm having a second longitudinal extent between a first end portion and second end portion thereof, such that the second base arm defines a second base arm axis; and a second clamp affixed to the second base arm at the first end portion thereof. The first base arm is fixed to the second base arm at their respective second end portions to form an angle between the first and second base arm axes, such that the first and second base arm axes cooperate to define a support plane, the support plane defining an X-Y plane of a Cartesian coordinate system. The device further includes a pair of handles each comprising a handle attachment portion defining a handle axis, a first of the pair of handles having a first handle configuration, and a second of the pair of handles having a second handle configuration; a riser having a third longitudinal extent defining a riser axis, the riser extending between a lower riser end and an opposed upper riser end, a lower ball joint pivotably connecting the attachment base to the lower riser end with an adjustable frictional engagement therebetween, the lower ball joint defining a neutral riser position in which the riser extends upwardly from the support plane in a Z-direction of the Cartesian coordinate system; an upper ball joint pivotably connecting the upper riser end to the handle attachment portion of either of the pair of handles with an adjustable frictional engagement therebetween, the upper ball joint defining a neutral handle position in which the handle axis and the riser axis are substantially parallel. The lower ball joint has a first degree of freedom in the X-direction and a second degree of freedom in the Y-direction, whereby the riser axis is moveable throughout a first spherical sector centered at the lower ball joint, and the upper ball joint has a third degree of freedom in the X-direction and a fourth degree of freedom in the Y-direction, whereby the handle axis is moveable throughout a second spherical sector centered at the upper ball joint.

In yet another form thereof, the present disclosure provides a method of training a patient using a soft tissue therapy device, the method including: configuring the soft tissue therapy device by one or more of the steps of mounting the soft tissue therapy device to a support surface and selecting a handle from among a plurality of interchangeable handles; adjusting a resistance level of an upper pivotable connection between an attachment base and a riser of the therapy device; adjusting a resistance level of a lower pivotable connection between the riser and the handle of the therapy device; and issuing at least one exercise command to a patient. The at least one exercise command includes an instruction to manipulate the soft tissue therapy device through a motion path centered around one or both of the upper and lower pivotable connections. The motion path is selected to target at least one soft tissue of the upper extremities of the patient. The resistance level of the upper and lower pivotable connections is selected to impart force to the at least one soft tissue at a desired level.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. Although the exemplifications set out herein illustrates an embodiment of the invention, the embodiment disclosed below is not intended to be exhaustive or to be construed as limiting the scope of the invention to the precise form disclosed.

DETAILED DESCRIPTION

Figure 1:
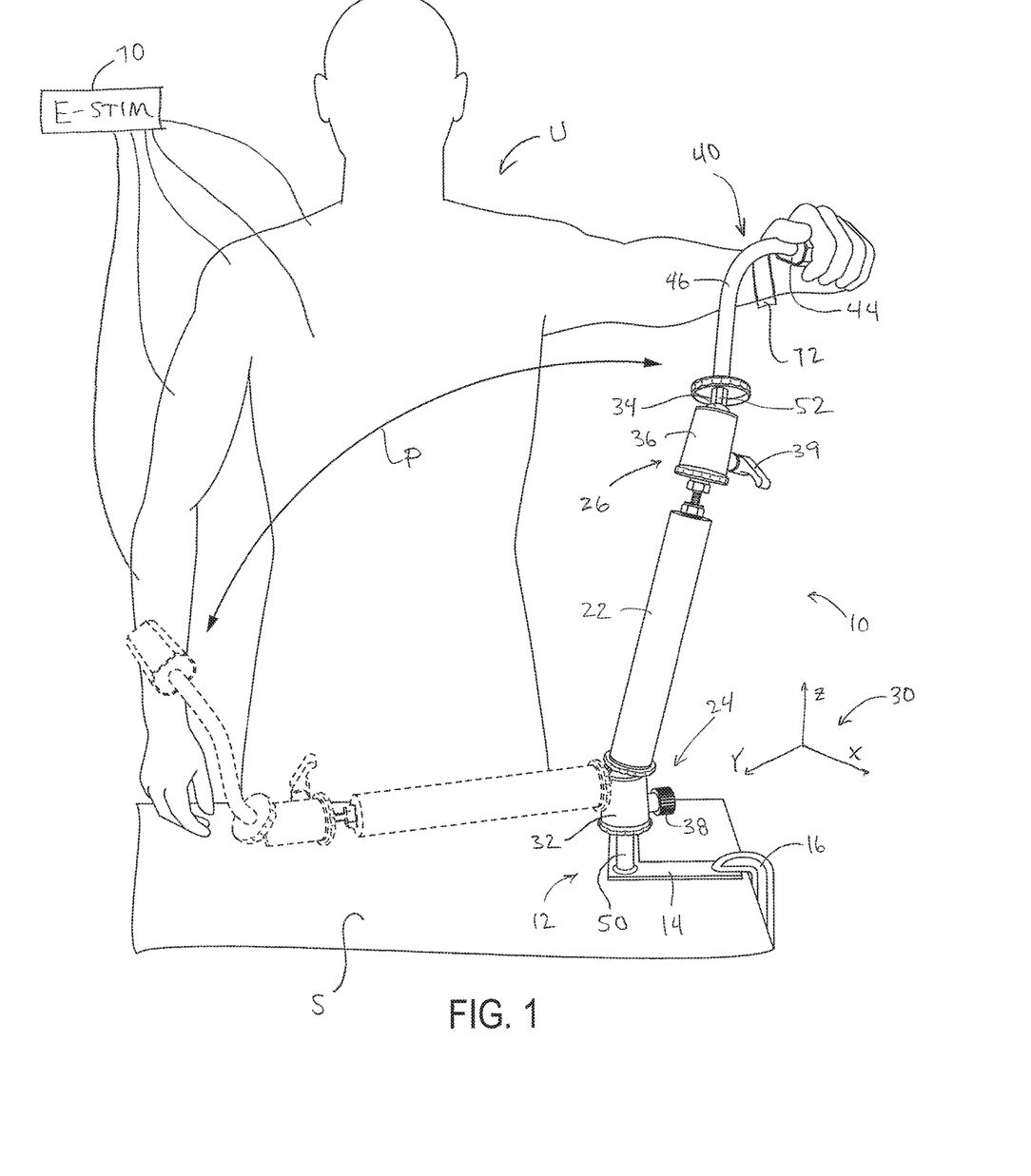
FIG. 1 is a perspective view of a therapy device made in accordance with present disclosure, illustrating one possible use of the device by a user.

The present disclosure provides soft tissue therapy device 10, shown in FIGS. 1-6, including attachment base 12, riser 22 pivotably connected to base 12 via a lower pivotable connection 24, and a user interface handle (e.g., single-grip handle 40 shown in FIG. 1 or double-grip handle 42 shown in FIG. 2) pivotably connected to riser 22 via upper pivotable connection 26. As described in detail below, the two pivotable connections 24, 26 are adjustable and combine with other adjustability to enable a wide range of motion paths P available to a user U (FIG. 1). This range of potential motions paths P allows therapy device 10 to be effectively leveraged for treatment of a wide variety of medical conditions pertaining to the upper extremities.

For purposes of the present disclosure, Cartesian coordinate system 30 is used to provide a frame of reference for the structures and motion paths of therapy device 10. In the illustrated embodiment, therapy device 10 is shown affixed to support surface S, which may be a table top surface, for example. Support surface S is considered to be substantially horizontal, such that a support surface plane defined by the table top surface an X-Y plane in Cartesian coordinate system 30. Various functional structures of therapy device 10, such as riser 22 and handle 40 or 42, extend upwardly from support surface S in a generally vertical direction, taken to be the Z direction of Cartesian coordinate system 30.

Figure 7:
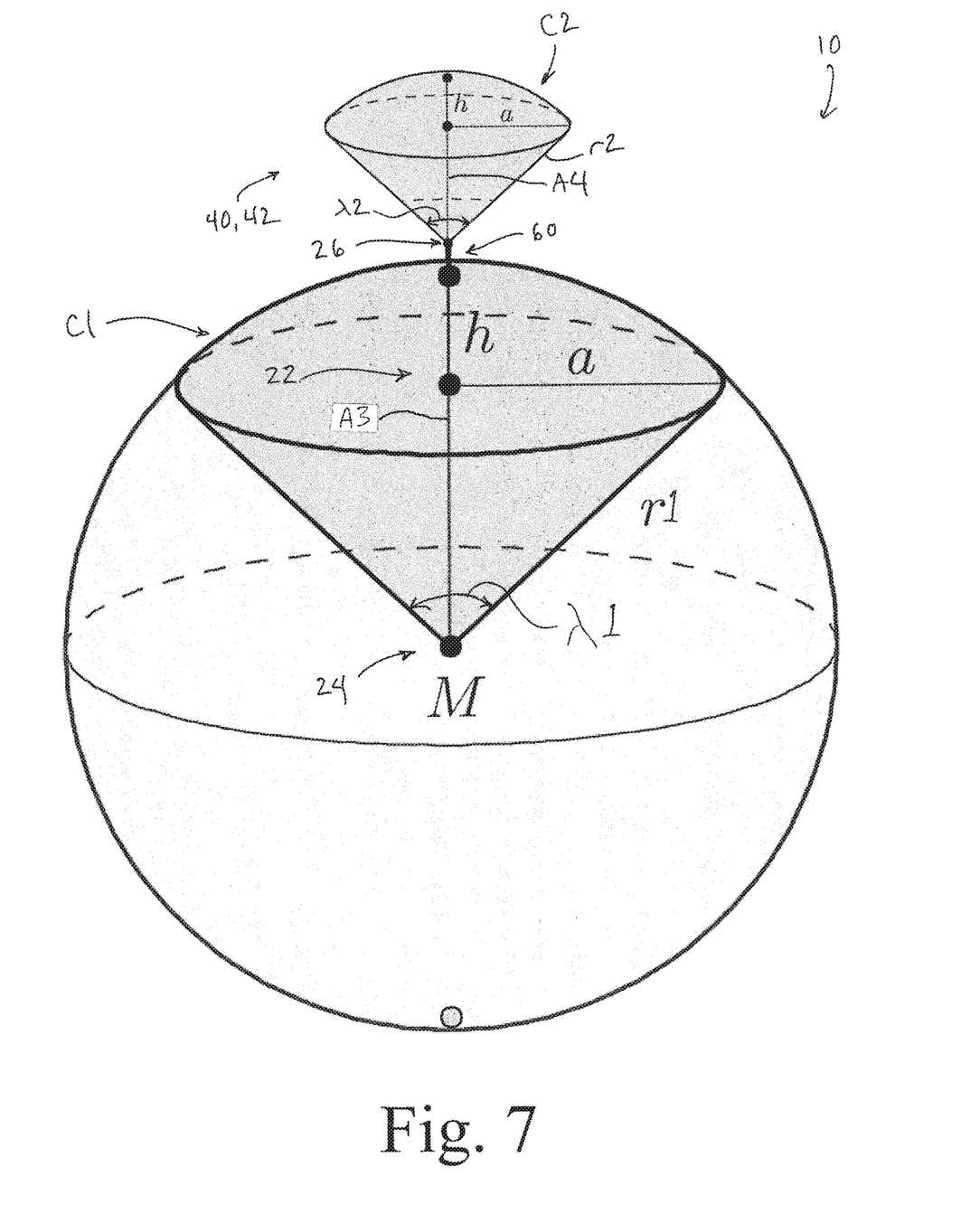
FIG. 7 is a schematic view of the therapy device shown in FIG. 3, illustrating the spherical sectors defined by the range of motion of the riser about the lower pivotable connection and the handle about the upper pivotable connection, respectively.

As described in detail below, device 10 may define a "neutral position" (FIG. 3) in which riser 22 and handle 40/42 both extend substantially vertically from support surface S. Riser 22 and handle 40/42 can be pivoted away from their neutral positions via lower pivotable connection 24 and upper pivotable connection 26, respectively. From the neutral position, riser 22 and handle 40/42 can angled with respect to the X and Y planes to any angled configuration within spherical sectors C1 and C2, respectively (FIG. 7).

1. Construction and Structures of the Therapy Device

Figure 2:
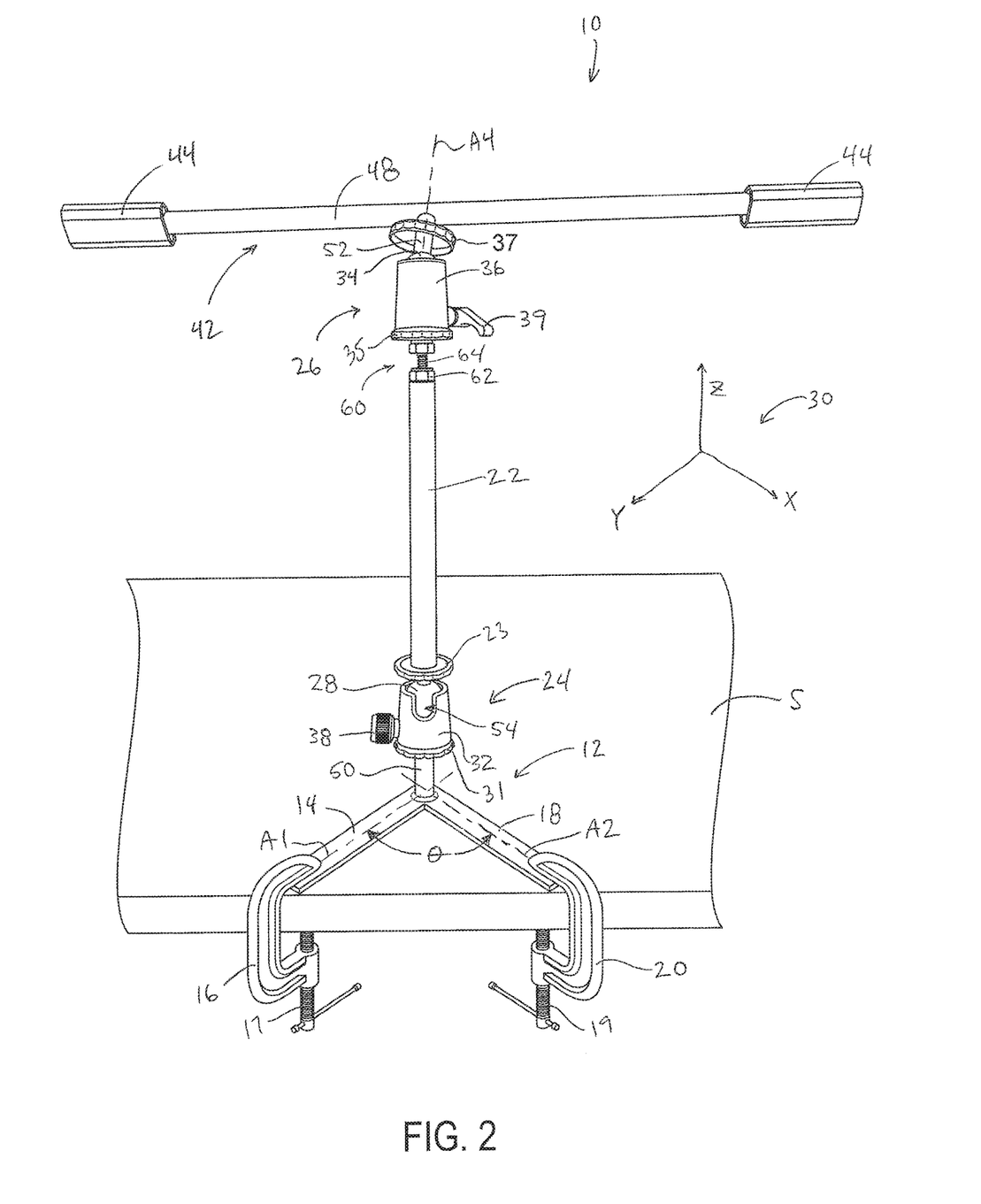
FIG. 2 is another perspective view of the therapy device shown in FIG. 1, illustrated with a double-grip handle in place of the single-grip handle shown in FIG. 1.
Figure 3:
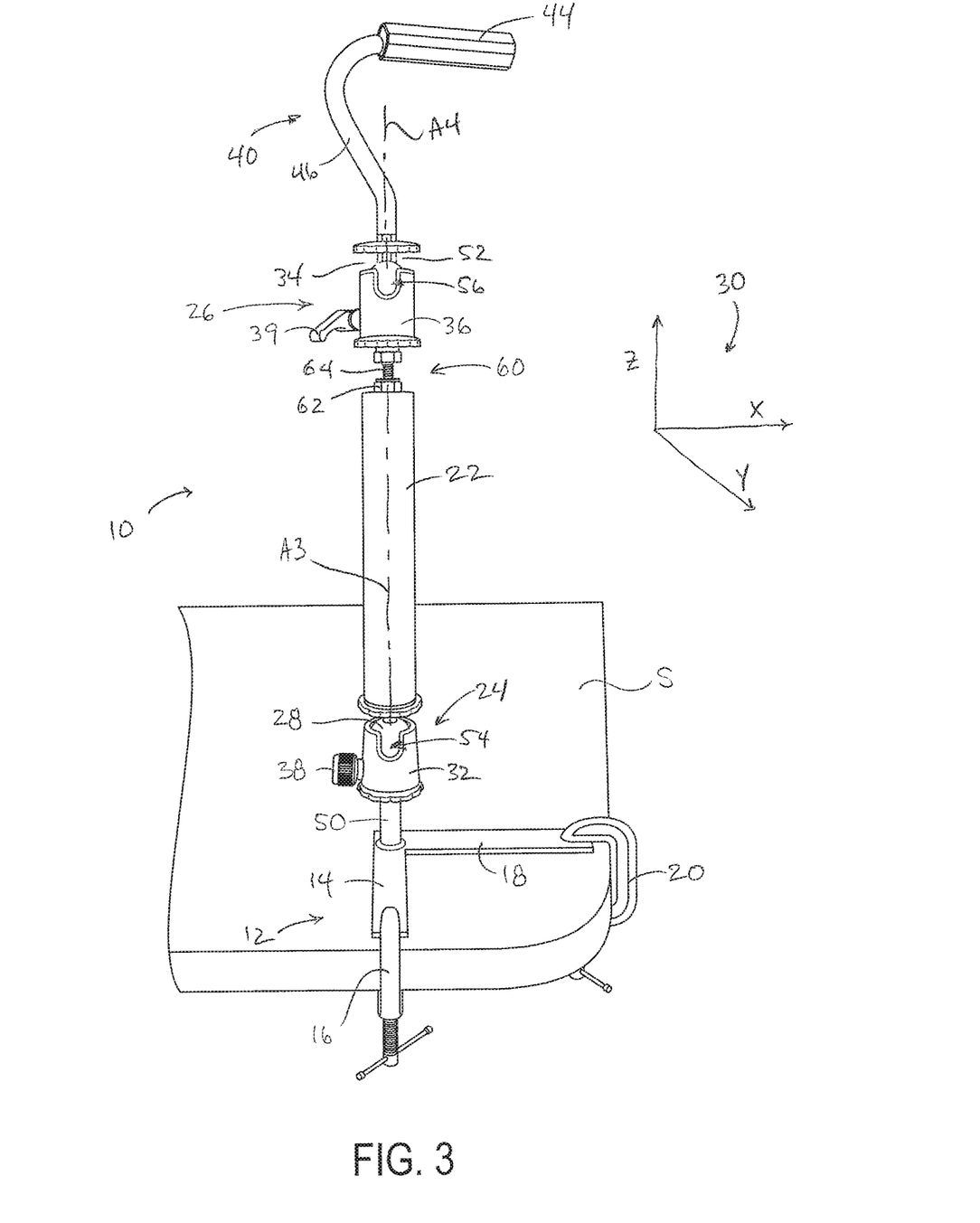
FIG. 3 is another perspective view of the therapy device shown in FIG. 1, in which the device is arranged in a neutral position.

As illustrated in FIG. 2, attachment base 12 is affixed to support surface S along a straight edge thereof, such as along the edge of a table, desk or other flat surface. Attachment base 12 includes a first base arm 14 formed as a generally longitudinal structure, illustratively, a flat elongated bar defining a longitudinal axis A1. Similarly, a second base arm 18 is illustratively formed from the same bar material as first base arm 14, and defines longitudinal axis A2. First and second base arms 14, 18 are joined at respective end portions thereof, e.g., by welding, to form angle θ between longitudinal axes A1 and A2. In an exemplary embodiment, angle θ may be about 90 degrees, which allows attachment base 12 to be modularly attached either to a straight table edge (FIG. 2) or a table corner (FIG. 3). However, it is appreciated than other acute and obtuse angles may be suitable for some applications.

Clamps 16 and 20 are fixed to the opposing free ends of first and second base arms 14, 18 respectively, e.g., by welding. In the illustrated embodiment, clamps 16 and 20 are standard C-clamp type devices with threaded rods 17, 19 which can be used to adjustably secure clamps 16, 20 to any surface or structure within their adjustable thickness range, such as surface S shown in FIG. 2. The overall structure and arrangement of attachment base 12 therefore allows for modular attachment to a wide variety of support surfaces, such that therapy device 10 can be used on a desktop for a sitting patient, a countertop for a standing patient, or any other suitable support surface.

Standoff 50 is affixed at the junction between base arms 14, 18 and extends upwardly therefrom in the Z direction. Base arms 14, 18 lie in an XY plane of Cartesian coordinate system 30, such that standoff 50 extends generally perpendicularly away from the support plane defined by axes A1, A2 of arms 14, 18. Lower socket 32, which forms the lower half of the ball-and-socket joint constituting the lower pivotable connection 24, is fixed to the upper end of lower standoff 50. In an exemplary embodiment, lower socket 32 includes a threaded stud extending downwardly into a correspondingly threaded hole in standoff 50, such that lower socket 32 can be raised and lowered with respect to attachment base 12 via the threaded connection. In order to fix lower socket 32 at a desired adjustment height, lock nut 31 may be threadably engaged with the threaded stud, and can be adjusted to bear against the upper surface of standoff 50 to lock the set height adjustment in place.

As noted above and shown in FIG. 2, riser 22 is pivotably attached to attachment base 12 via the lower ball-and-socket connection 24. In particular, ball 28 is received within a correspondingly spherical cavity formed within socket 32 and is adjustably frictionally secured therein via friction adjuster 38. In the illustrated embodiment, friction adjuster 38 may be used to allow ball 28 to freely move within socket 32, or to lock ball 28 within socket 32 such that lower pivotable connection 24 is selectively non-functional. Friction adjuster 38 may also be adjusted to impart any desired amount of frictional engagement with socket 32, such that ball 28 may move within socket 32 under sufficient force to overcome the friction. In this way, the force required to pivot riser 22 through its range of motion may be adjusted as required for a particular use or application.

Riser 22 is threadably fixed to ball 28, such that pivoting riser 22 within its range of motion also pivots ball 28 within socket 32. In an exemplary embodiment, riser 22 may be vertically adjusted with respect to ball 28 via lock nut 23, which operates similarly to lock nut 31 described above. In the illustrated embodiment, ball 28 includes a threaded stud engaged with a correspondingly threaded hole in riser 22.

Handle 40 (FIG. 3) or 42 (FIG. 2) is pivotably attached to the upper end of riser 22 via upper pivotable connection 26, which is formed by an upper ball joint including ball 34 and socket 36. In particular, socket 36 is threadably fixed to the upper end of riser 22, and may be adjusted via the height adjustment assembly 60 including stop nut 62 and height adjustment stud 64. Ball 34 is threadably affixed to handle 42 via standoff 52. As with other connections of therapy device 10 described herein, height adjustment assembly 60 and lock nut 37 may be used for vertical adjustment, such that upper pivotable connection 26 may be vertically adjusted with respect to riser 22 and handle 40/42 may be vertically adjusted with respect to upper pivotable connection 26.

Similar to lower ball joint 24, upper ball joint 26 includes friction adjuster 39 which may be used to selectively loosen or tighten the frictional engagement between socket 36 and ball 34, such that the force required to pivot handle 40/42 through its range of motion may be adjusted as required for a particular use or application. Additionally, friction adjuster 39 may be tightened to the point where ball 34 is effectively locked within socket 36, such that upper pivotable connection 26 is selectively non-functional.

Friction adjuster 39 may also enable interchangeability of handles 40 and 42. For example, where it is desired to exchange the single-grip handle 40 (FIG. 1) for the double-grip handle 42 (FIG. 2), adjuster 39 can be loosened sufficiently to allow ball 34 to be completely withdrawn from socket 36. Handle 40 may then be set aside, together with ball 34 and standoff 52. Handle 42, which may have its own standoff 52 and ball 34 already attached, may then be installed by placing ball 34 within socket 36 and retightening upper friction adjuster 39. Other designs of handles may similarly be provided and may be modularly attachable and detachable as required or desired for particular therapies or applications.

In the illustrative embodiment of FIG. 2, handle 42 includes a pair of handgrips 44 disposed at either end of a substantially straight bar 48. Bar 48 is substantially perpendicular to standoff 52, which has a longitudinal axis parallel or coaxial with axis A3 of riser 22 in a "as further described below. Thus, in this neutral configuration, the substantially straight bar 48 is generally parallel with support surface S and the XY support plane, while standoff 52 is generally upright and vertical along the Z direction.

Curved handle 40, shown in FIG. 3, includes a curved bar 46 which has a lower portion straight portion generally coaxial with standoff 52 and an upper curved portion which completes a 90 degree bend between standoff 52 and handgrip 44. Therefore, when therapy device 10 is in the neutral configuration, the lower straight portion of handle 40 is generally upright and vertical along the Z direction, while the longitudinal axis of handgrip 44 is generally parallel with support surface S and the XY support plane.

FIG. 3 illustrates therapy device 10 in a fully neutral configuration and including single-grip handle 40. In this fully neutral configuration, riser 22 is upright and vertical along the Z direction, such that the riser longitudinal axis A3 is generally coaxial with a corresponding longitudinal axis of standoff 50 and perpendicular to support surface S and the XY support plane. In addition, ball 28 of the lower ball-and-socket connection 24 is generally centered within lower socket 32, such that ball 28 can angularly displace equally in any direction relative to the XY support plane (with the exception of a large angular displacement enabled by socket slot 54, as further described below).

Similarly, ball 34 of the upper ball-and-socket connection 26 is also shown centered within socket 36 in the fully neutral configuration of FIG. 3, such that ball 34 can angularly displace equally in any direction relative to axis A3 of riser 22 (with the exception of a large angular displacement enabled by socket slot 56, as further described below). Standoff 52, which extends along longitudinal axis A4 of handle 40, is generally upright and vertical along the Z direction, and is therefore generally coaxial with the riser axis A3 and the axis of standoff 50. Axis A4 of handle 40 is therefore also generally perpendicular to support surface S and the XY support plane.

Lower pivotable connection 24 and upper pivotable connection 26 allow axes A3 and A4, respectively, to be angularly displaced along both the X and Y direction. The range of angular displacement of axis A3 will be described in detail below, it being understood that axis A4 displaced similarly except as otherwise noted.

Axis A3 has a first degree of freedom in the X direction and second degree of freedom in the Y direction, such that the riser axis A3 is movable throughout a first spherical sector centered at the lower pivotable connection 24, as schematically illustrated in FIG. 7 by spherical sector C1. Spherical sector C1 is formed by a cone with a partial sphere joined to the base of the cone, with a radius R1 equal to the total axial distance between the lower and upper pivotable connections 24, 26. This distance may change depending on vertical adjustments, such as via height adjustment assembly 60 shown in FIG. 7.

Figure 4:
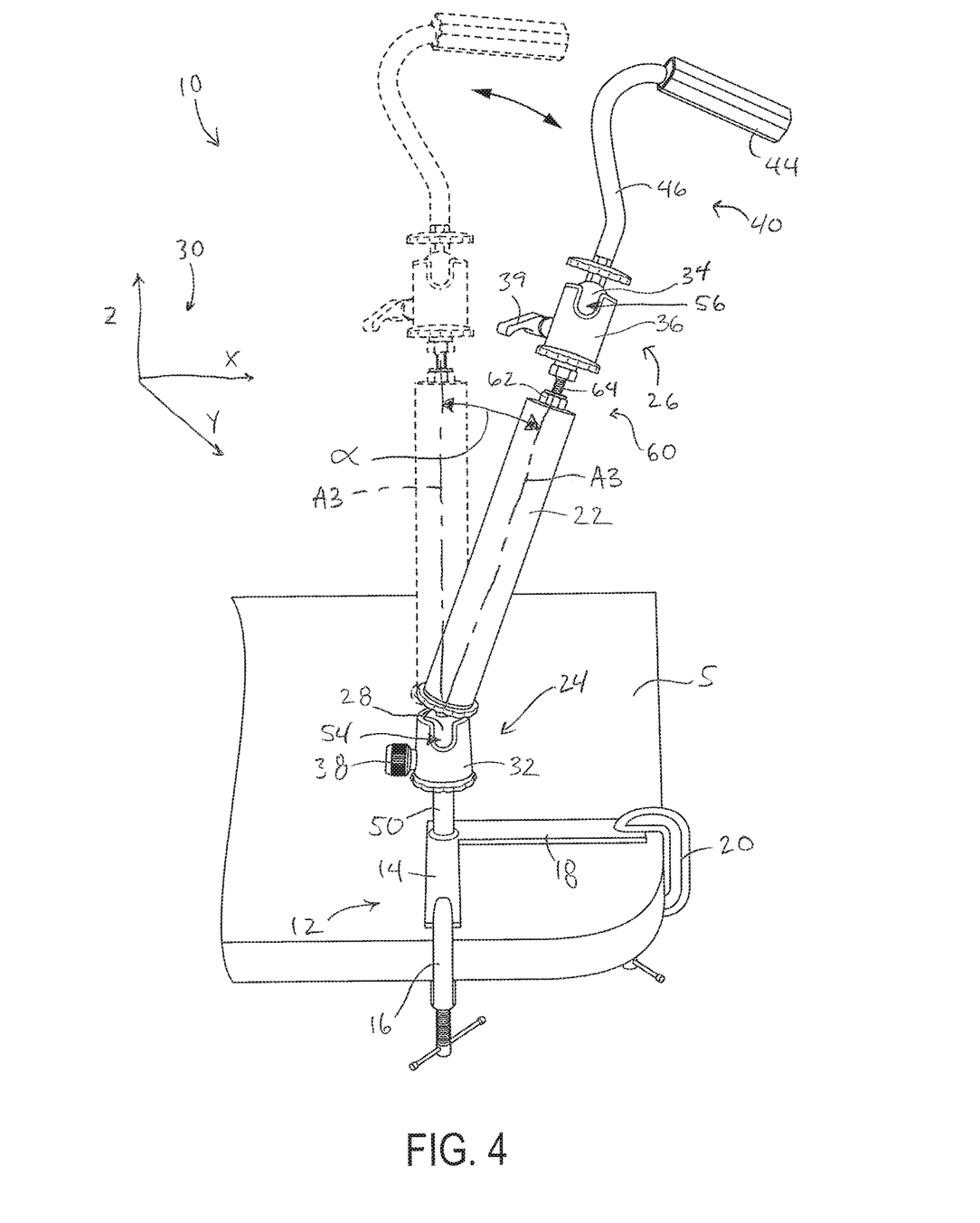
FIG. 4 is another perspective view of the therapy device shown in FIG. 3, in which the riser of the device is angled away from the neutral position about the lower pivotable connection, while the handle maintains its neutral position relative to the riser.

In FIG. 4, axis A3 is shown angularly displaced by angle α, while handle 40 remains in its nominal neutral position with respect to riser 22. In the illustrated embodiment, angle α may be up to about 45 degrees, 60 degrees, 75 degrees or even 90 degrees, depending on the structure and arrangement of lower pivotable connection 24. The overall included angle λ1 of sector C1, which represents the total angular adjustment available to riser 22, is equal to twice the maximum angular displacement from the neutral configuration, i.e., $\lambda 1 = (2 * \alpha)$.

Figure 6:
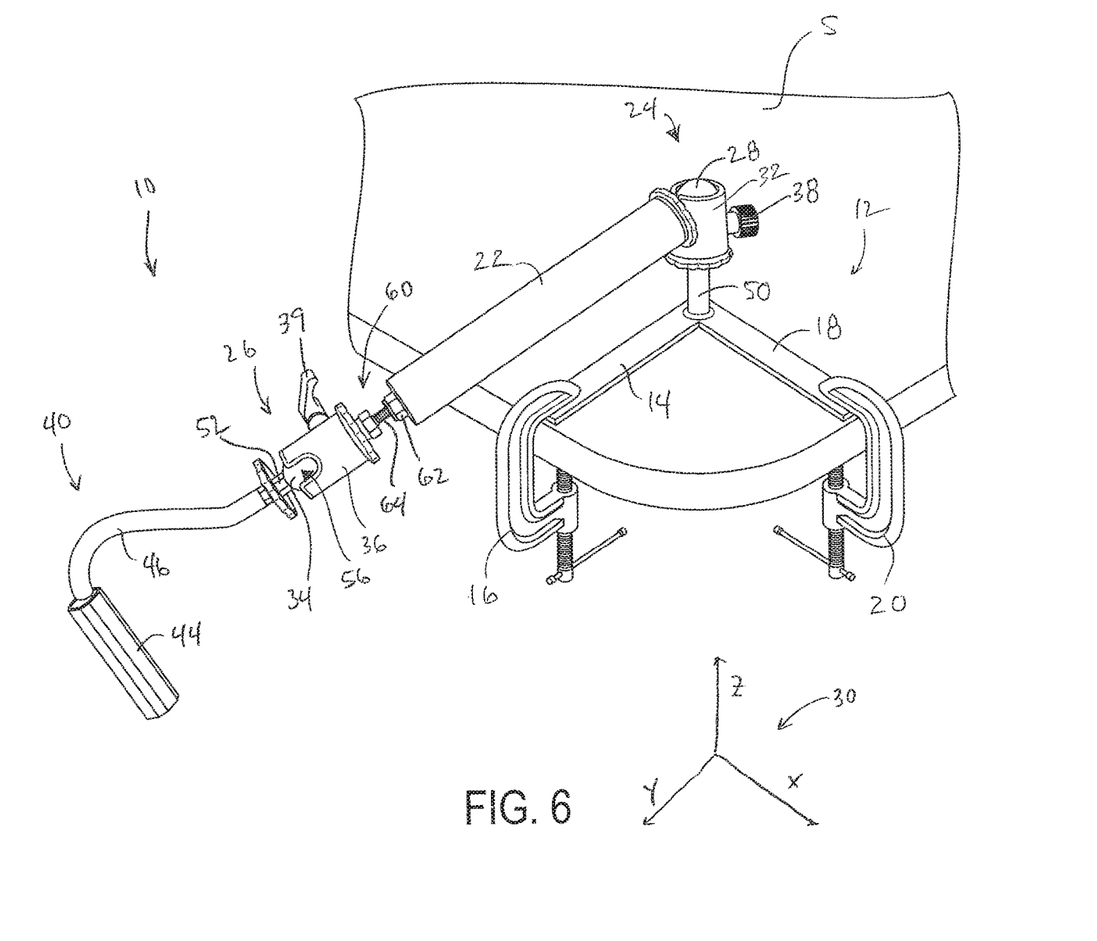
FIG. 6 is another perspective view of the therapy device shown in FIG. 3, in which the riser is pivoted 90 degrees from neutral.

In at least one rotational orientation, slot 54 is provided in socket 32 to allow a larger angular displacement α than may be available in the other rotational orientations for a ball-and-socket joint (which, in the illustrated embodiment, offer less than 90 degrees of angular displacement from neutral). As shown in FIG. 6, riser 22 may be allowed to pivot by as much as 90 degrees or greater as the threaded stud extending from ball 28 is allowed to traverse slot 54 while ball 28 remains retained by the rest of socket 32. As further discussed below, this deep-angle functionality may be beneficial for some therapeutic applications.

Figure 5:
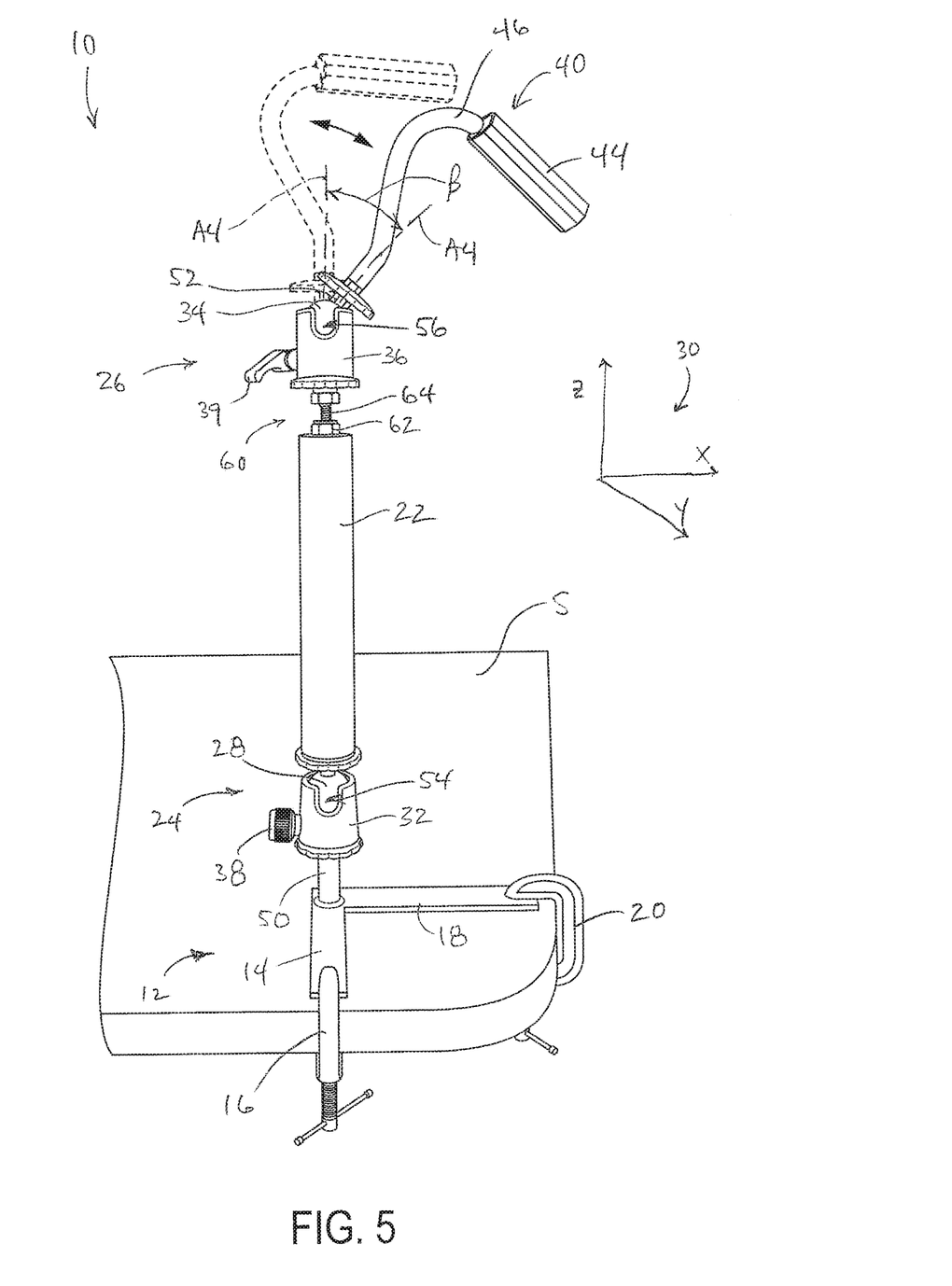
FIG. 5 is another perspective view of the therapy device shown in FIG. 3, in which the handle of the device is pivoted away from the neutral position about the upper pivotable connection, while the riser maintains its neutral position relative to the attachment base.

Turning now to FIG. 5, handle 40 is shown pivoted away from its neutral position while riser 22 remains in its neutral position. Similar to the pivoting of riser 22, handle 40 has two degrees of freedom arising from pivotable connection 26, herein referred to as a "third" degree of freedom in the X direction and a "fourth" degree of freedom in the Y direction, in order to distinguish these degrees of freedom from the "first" and "second" degrees of freedom pertaining to riser 22. For purposes of the present disclosure, a neutral position of handle 40 is considered to be when axis A4 of handle 40 is substantially coaxial or parallel to axis A3 of riser 22, regardless of whether riser 22 is in a neutral or pivoted position.

Axis A4, which is generally shorter than axis A3 in the illustrated embodiments in which handles 40, 42 have smaller vertical extents as compared to riser 22, defines spherical sector C2 (FIG. 7) centered about upper pivotable connection 26. An included angle λ2 of spherical sector C2 is twice the maximum angular deflection β permitted by upper pivotable connection 26 (i.e., λ2=β*2), similar to the relationship between angles α and λ1 of pivotable connection 24. Upper socket 36 includes at least one socket slot 56 to allow for a greater angular deflection of axis A4 at a designated rotational position, similar to the structure and function of lower socket slot 54 described above.

In addition to the two degrees of freedom in the X and Y directions for lower and upper pivotable connections 24 and 26 described above, the ball-and-socket joints illustrated in FIGS. 1-6 also afford one additional degree of freedom for each of connections 24 and 26. In particular, lower pivotable connection 24 includes a "fifth" degree of freedom of rotation about the Z direction, such that riser 22 may "spin" about its axis A3. Similarly, upper pivotable connection 26 includes a "sixth" degree of freedom of rotation about riser axis A3, such that handle 40 or 42 may "spin" about its longitudinal axis A4.

Although ball-and-socket joints effectively and efficiently provide three degrees of freedom for each of the lower and upper pivotable connections 24, 26, it is contemplated that other pivotable connections may be employed for therapy device 10 as required or desired for a particular application. For example, a U-joint type connection pivotably mounted to attachment base 12 (e.g. by a pivot pin received in standoff 50) would also provide three degrees of freedom for lower pivotable connection 24 in similar fashion to the illustrated ball-and-socket connection.

Any other suitable pivot joint may be employed where at least the X and Y degrees of freedom are provided, with the rotational degree of freedom being optionally provided. Any combination of pivot joint designs, such as one U-joint and one ball-and-socket joint, may be employed in therapy device 10.

2. Use and Therapeutic Applications of the Therapy Device.

In use a patient, shown as user U in FIG. 1, may grasp the handgrip 44 (or pair of handgrips 44). Pursuant to at least one exercise command from an occupational therapist or other trained professional, user U may then actuate therapy device 10 along a designated motion path P, actuating one or both pivotable connections 24, 26 as dictated by the particularities of path P. As described in further detail below, the occupational therapist or other trained professional instructing user U may configure and adjust soft tissue therapy device 10 in order to promote a particular desired outcome or set of outcomes based on the therapist's professional assessment of the needs of the induvial user U.

Prior to use by user U, a therapist can configure therapy device 10 in view of the particular therapies to be administered and therapeutic outcomes desired. As in initial setup step, the therapist may choose a support surface S for mounting therapy device 10. As noted above, attachment base 12 may be fixed to support surface S along a straight surface edge, as shown in FIG. 2, or at a surface corner as shown in FIG. 3. The height of support surface S may also be chosen based on whether the user U will be standing or sitting during the exercise. With therapy device 10 positioned as desired, clamps 16, 20 may be actuated in order to securely affix therapy device 10 to support surface S.

Next, a therapist may adjust the friction at lower pivotable connection 24 and/or at upper pivotable connection 26. In most cases, only a single pivotable connection may be desired, while the other pivotable connection is locked. However, it is contemplated that in other cases, both pivotable connections may be implicated in the desired motion path P (FIG. 1). In either case, the amount of resistance offered to user U in actuating therapy device 10 through motion path P may be adjusted by tightening or loosening the user-accessible, manually operable friction adjusters 38, 39 as desired.

The therapist may then summon user U to therapy device 10, with an instruction to grasp the handgrip or handgrips 44 and execute at least one exercise command to effect motion path P. The resistance level chosen for lower and upper pivotable connections 24, 26 dictates the nature of motion path P, and the force imparted to the soft tissues of user U during execution of the therapist's instruction.

In exemplary methods of instruction, motion path P requires no more than two exercise commands, thereby avoiding or mitigating user confusion and encouraging effective and proper form in the user's execution of the therapist's exercise command(s). Maintaining a focus on motions which require only 1 or 2 exercise commands is particularly beneficial for patients with cognitive impairments, Traumatic Brain Injury (TBI), or other conditions affecting the memory or ability to maintain attention or focus (e.g., Alzheimer's or forms of dementia).

Motion path P may incorporate unilateral motions, which generally require single-grip handle 40, or bilateral motions, which generally require double-grip handle 42 (FIG. 2). One of handles 40 or 42 may be selected and installed to device 10 as part of the setup configuration, depending on whether unilateral or bilateral motions are to be performed.

The particular motion path P and the attendant setup of soft tissue therapy device 10 may be selected in view of the upper extremity or extremities involved in the therapy, the muscles of the patient sought to be trained, and the functional tasks sought to be enhanced. Potential functional tasks implicated in the use of therapy device 10 include, but are not limited to, eating, grooming and hygiene tasks, dressing, laundry, toileting, transfers, standing tolerance, hobbies or activities of interest for a particular user U, and driving. Soft tissues of interest include joints, tendons, and muscles of the upper extremities, including shoulders, elbows and wrists.

Therapeutic outcomes pertaining to such soft tissues include increased strength, increased range of motion (ROM) and increased muscular endurance.

In connection with these goals, some uses of therapy device 10 may relate to neuromuscular reeducation following a loss of coordination of movements, impaired balance, and general lack of control which may occur with some disorders and injuries. Such neuromuscular reeducation uses may include a choice of motion path P which enhances dynamic or static standing balance. This may be accomplished, for example, by proprioceptive neuromuscular facilitation (PNF) stretching, which is a set of stretching techniques designed to enhance active and passive range of motion by a shortening contraction of the opposing muscle to place the target muscle in a PNF stretch, followed by an isometric contraction of the target muscle. Additional therapeutic outcomes may include enhanced righting reactions (i.e., promoting the correct orientation of the head and body with respect to the vertical) and proper postural alignment.

As will be understood by persons of skill in the art of occupational therapy, the above described therapeutic techniques and outcomes may be sought with a wide range and combination of motion paths P, all of which may be articulated using various configurations and adjustments of therapy device 10. The particular configuration, setup and instruction for use of device 10 can be expected to vary depending on the needs and condition of each individual user U.

In addition to setup and configuration of therapy device 10, additional therapies may be combined with device 10 to further enhance patient outcomes. In one embodiment, an electrical muscle stimulation ("e-stim") device 70 may be connected to user U at the time of actuation of soft tissue therapy device 10. E-stim device 70 may be electrically connected to one or more target muscles of the upper extremities, including those of the forearm, upper arm, chest, shoulders or back of the user U. When activated, e-stim device 70 induces a muscular response which can be observed and controlled during actuation of therapy device 10 in order to correct or hypertonicity or hypotonicity of the affected extremity or extremities. The desired outcome of such therapies may be to encourage normal patterns of movement, for example. Alternatively, a therapist may utilize the "muscle belly tapping" therapeutic technique to accomplish a comparable muscular effect as e-stim device 70.

In addition to adjustment of the resistance level via friction adjusters 38, 39 as described above, further adjustment or grading of the resistance encountered by user U during therapeutic exercises may be effected through the use of weights connected to the upper extremities of user U, such as wrist weights 72 as shown in FIG. 1. Such weights may increase resistance in addition to, or in lieu of, resistance adjustments of pivotable connections 24, 26 via friction adjusters 38, 39 respectively.

Yet another adjustment to the therapeutic exercises of therapy device 10 may be accomplished by the position and posture of user U during exercises, particularly with regard to whether user U is standing or sitting. If user U preforms the exercises directed by the therapist while standing, both the neuromuscular and biomechanical frames of reference may be challenged simultaneously. In connection with this adjustment, the therapist may choose mounting surface S based on its height above the ground and relative to a patients support such as a chair or bench.

3. Applications.

As noted above, soft tissue therapy device 10 may be used for a wide variety of patients having a wide variety of medical conditions or including injuries and disorders.

In one application, therapy device 10 may be used to treat patients with cognitive disorders including dementia and Alzheimer's. Exercise directives from the therapist may incorporate relatively simple unilateral or bilateral motions as noted above, to allow the patient to complete a therapeutic exercise with minimal confusion or frustration due to the exercise being preserved as unduly complicated or involving excessive steps.

In another application, a patient who has had a cerebrovascular accident (CVA), commonly referred to as a stroke, may regain the use of one or more upper extremities via "retraining" of the affected muscles through use of therapy device 10. Similarly, patients with Traumatic Brain Injury (TBI), which is an intracranial injury occurring when an external force injures the brain, may also regain the effective use of upper extremities using therapy device 10. As with other cognitive impairments discussed herein, the simplicity of movements and repetition using soft tissue therapy device 10 facilitates the therapeutic exercises needed for such recovery.

Still other applications include treatment of neuromuscular disorders such as Parkinson's disease, characterized by a lack of control with coordinated movements, impaired balance, and stuffiness of the limbs and trunk. The general constraints on motion paths P via therapy device 10, together with the modularity of its configuration and use, allows for the varied complications of Parkinson's to be addressed by the therapist.

Yet another application of therapy device 10 includes certain rare or uncommon medical diagnoses, such as Guillain-Barre's syndrome, characterized by weakening of muscles due to autoimmune response. Patients with such diagnoses can benefit from using therapy device 10 to increase strength, range of motion, and endurance of the upper extremities for improved independence with activities of daily living, including the functional tasks outlined above.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of appended claims.

What is claimed is:

1. A soft tissue therapy device for use with upper extremities of patient, the device comprising:
   an attachment base comprising:
   a first base arm having a first longitudinal extent between a first end portion and second end portion thereof, such that the first base arm defines a first base arm axis;
   a first clamp affixed to the first base arm at the first end portion thereof;
   a second base arm having a second longitudinal extent between a first end portion and second end portion thereof, such that the second base arm defines a second base arm axis; and
   a second clamp affixed to the second base arm at the first end portion thereof,
   the first base arm fixed to the second base arm at their respective second end portions to form an angle between the first and second base arm axes, such that the first and second base arm axes cooperate to define a support plane, the support plane defining an X-Y plane of a Cartesian coordinate system;

a handle comprising a handle attachment portion defining a handle axis and at least one grip portion spaced from the handle attachment portion; and a riser having a third longitudinal extent defining a riser axis, the riser extending between a lower riser end and an opposed upper riser end, the lower riser end having a lower pivotable connection to the attachment base, the lower pivotable connection defining a neutral riser position in which the riser extends upwardly from the support plane in a Z-direction of the Cartesian coordinate system, the upper riser end having an upper pivotable connection to the handle, the upper pivotable connection defining a neutral handle position in which the handle axis and the riser axis are parallel, the lower pivotable connection having a first degree of freedom in the X-direction and a second degree of freedom in the Y-direction, whereby the riser axis is moveable throughout a first spherical sector centered at the lower pivotable connection, and the upper pivotable connection having a third degree of freedom in the X- direction and a fourth degree of freedom in the Y-direction, whereby the handle axis is moveable throughout a second spherical sector centered at the upper pivotable connection.

2. The soft tissue therapy device of claim 1, wherein the lower pivotable connection further comprises a fifth degree of freedom of rotation about the Z-direction of the Cartesian coordinate system.

3. The soft tissue therapy device of claim 1, wherein the upper pivotable connection further comprises a sixth degree of freedom of rotation about the riser axis.

4. The soft tissue therapy device of claim 1, wherein the riser is pivotable up to 90 degrees from its neutral position.

5. The soft tissue therapy device of claim 1, wherein the handle is pivotable up to 90 degrees from its neutral position.

6. The soft tissue therapy device of claim 1, wherein the lower pivotable connection comprises a lower ball joint comprising:
a lower ball fixed to one of the attachment base and the riser; and
a lower socket fixed to the other of the attachment base and the riser.

7. The soft tissue therapy device of claim 6, wherein the lower socket is adjustably compressible about the lower ball, whereby the riser is adjustably frictionally engaged with the attachment base.

8. The soft tissue therapy device of claim 1, wherein the upper pivotable connection comprises an upper ball joint comprising:
an upper ball fixed to one of the riser and the handle;
an upper socket fixed to the other of the riser and the handle.

9. The soft tissue therapy device of claim 8, wherein the upper socket is adjustably compressible about the upper ball, whereby the handle is adjustably frictionally engaged with the riser.

10. The soft tissue therapy device of claim 1, wherein the at least one grip portion of the handle comprises a single handgrip joined to the handle attachment portion by a curved bar.

11. The soft tissue therapy device of claim 1, wherein the at least one grip portion of the handle comprises a pair of handgrips joined to one another by a substantially straight bar, the substantially straight bar substantially perpendicular to the handle axis.

12. A soft tissue therapy device for use with upper extremities of patient, the device comprising:
an attachment base comprising:
a first base arm having a first longitudinal extent between a first end portion and second end portion thereof, such that the first base arm defines a first base arm axis;
a first clamp affixed to the first base arm at the first end portion thereof;
a second base arm having a second longitudinal extent between a first end portion and second end portion thereof, such that the second base arm defines a second base arm axis; and
a second clamp affixed to the second base arm at the first end portion thereof,
the first base arm fixed to the second base arm at their respective second end portions to form an angle between the first and second base arm axes, such that the first and second base arm axes cooperate to define a support plane, the support plane defining an X-Y plane of a Cartesian coordinate system;

a pair of handles each comprising a handle attachment portion defining a handle axis, a first of the pair of handles having a first handle configuration, and a second of the pair of handles having a second handle configuration;

a riser having a third longitudinal extent defining a riser axis, the riser extending between a lower riser end and an opposed upper riser end, a lower ball joint pivotably connecting the attachment base to the lower riser end with an adjustable frictional engagement therebetween, the lower ball joint defining a neutral riser position in which the riser extends upwardly from the support plane in a Z-direction of the Cartesian coordinate system; and an upper ball joint pivotably connecting the upper riser end to the handle attachment portion of either of the pair of handles with an adjustable frictional engagement therebetween, the upper ball joint defining a neutral handle position in which the handle axis and the riser axis are parallel, the lower ball joint having a first degree of freedom in the X-direction and a second degree of freedom in the Y-direction, whereby the riser axis is moveable throughout a first spherical sector centered at the lower ball joint, and the upper ball joint having a third degree of freedom in the X-direction and a fourth degree of freedom in the Y-direction, whereby the handle axis is moveable throughout a second spherical sector centered at the upper ball joint.

13. The soft tissue therapy device of claim 12, wherein:
the first handle configuration comprises a curved bar having a first end fixed to the handle attachment portion and second end fixed to a hand grip; and
the second handle configuration comprises substantially straight bar having a first end fixed to a first hand grip, a second end fixed to a second hand grip, and a central portion between the first and second ends fixed to the handle attachment portion.

14. The soft tissue therapy device of claim 12, wherein the lower ball joint comprises a lower socket adjustably frictionally engageable with a lower ball by a first user-accessible adjuster, and the upper ball joint comprises an upper socket adjustably frictionally engageable with an upper ball by a second user-accessible adjuster.

15. The soft tissue therapy device of claim 12, wherein the riser is pivotable up to 90 degrees from its neutral position and at least one of the pair of handles is pivotable up to 90 degrees from its neutral position.

\* \* \* \* \*